United States Patent [19]

Klionsky et al.

[11] Patent Number: 5,587,290

[45] Date of Patent: Dec. 24, 1996

[54] STRESS TOLERANT YEAST MUTANTS

[75] Inventors: Daniel Klionsky, Davis, Calif.; Helmut Holzer; Monika Destruelle, both of Freiburg, Germany

[73] Assignee: The Regents of the University of California, Oakland, Calif.

[21] Appl. No.: 494,714

[22] Filed: Jun. 26, 1995

[51] Int. Cl.$^6$ .............................. C12Q 1/68; C12N 1/19; C12N 15/31

[52] U.S. Cl. .................. 435/6; 435/7.31; 435/172.1; 435/254.21; 435/255.2; 536/23.74

[58] Field of Search ..................... 435/6, 254.2, 172.1, 435/254.21, 7.31, 255.2; 536/23.1, 23.74

[56] References Cited

PUBLICATIONS

Nwaka et al., *FEBS Letters*, vol. 360, 6 Mar. 1995, pp. 286–290.

Destruelle, PhD Thesis, Faculty of Biology, University of Freiburg, Germany, 1993.

*Primary Examiner*—James S. Ketter
*Attorney, Agent, or Firm*—Richard Aron Osman

[57] ABSTRACT

The invention provides methods and compositions relating to stress tolerant yeast; in particular, yeast mutants deficient in the expression of functional ATH1 gene product (Ath1p). Such yeast have enhanced tolerance to dehydration and freezing, are able to grow to a higher cell density over a range of fermentable carbon source concentrations, are able to produce and/or tolerate higher levels of ethanol, and trehalose. Nucleic acids comprising ATH1 gene sequences are used in hybridization probes and PCR primers, in expression vectors, etc. The invention provides methods for producing a yeast mutant with improved survival ability under stress conditions which involve identifying mutations disrupting ATH1 expression using Ath1-specific reagents or ATH1 hybridization probes or primers.

9 Claims, 4 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3876 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 579..3701

( x i ) SEQUENCE DESCRIPTION: SEQ ID NO:1:

```
GTCGTTATTG  AATAATAATA  ACAAAATTTC  TCCACTTTTC  ACCATATTAC  CACTCCCTTT         60
```

| | |
|---|---|
| TTTTCAAGTA AAAAAAAAAA AAAAAAGAAT CTTATTGCTC CTTAAAAAAG GATTCATCAG | 120 |
| TCCTTTATGA GGCCTGCTAG TATCACCTAA TATTGCATCT GTTTTTACCG AAATTTCCTC | 180 |
| ATTCCAATAA TGAAAGAAT AAGATCGCTT TGGTTCAATG CGGAGGCTTC TTATTCAAAC | 240 |
| CTTAACAATT CTCCTAGTTT GAGGAACAAA AATAGTACCG GTAATAACTC TCGCTCTAAA | 300 |
| AATTATCGTT CTTTCTCAAG GTTTGACTTG ATCAACTCTA TACTTTTACT GATGATGCTA | 360 |
| TTTTTATTAG CTATCTTCGT CACTGCATTA TATTTAACAA AGCGTTCCAG GCTTACATAC | 420 |
| TCACATGCCT CGAGGGCTGC CCTATTTAAC CTCTGGGTGT GATATCGCCG TCATTGGGAA | 480 |
| ATCATACGTT GAACTACGAT CCAGAAGCAA GGGAATCTTC TAAAAAACTT TATGAACTCC | 540 |
| TTTCTGATTT CAACACGGCA TATTATGATG ATGAGAAC ATG ATT TTG GGA AGT | 593 |
|                                                       Met Ile Leu Gly Ser<br>                                                       1                  5 | |
| AAC TTG TTC TCA AAG AAT ACA TAC TCG AGA CAA CCA TAT GTT GCT AAC<br>Asn Leu Phe Ser Lys Asn Thr Tyr Ser Arg Gln Pro Tyr Val Ala Asn<br>               10                       15                      20 | 641 |
| GGT TAT ATA GGT AGT CGT ATT CCC AAT ATT GGG TTC GGC TAT GCC TTA<br>Gly Tyr Ile Gly Ser Arg Ile Pro Asn Ile Gly Phe Gly Tyr Ala Leu<br>               25                       30                      35 | 689 |
| GAC ACC CTG AAT TTT TAC ACA GAC GCA CCA GGC GCT TTG AAT AAC GGT<br>Asp Thr Leu Asn Phe Tyr Thr Asp Ala Pro Gly Ala Leu Asn Asn Gly<br>           40                         45                      50 | 737 |
| TGG CCC TTA AGA AAT CAT AGA TTT GCC GGT GCG TTT GTA TCG GAC TTT<br>Trp Pro Leu Arg Asn His Arg Phe Ala Gly Ala Phe Val Ser Asp Phe<br>     55                       60                      65 | 785 |
| TAT TGT CTA CAA CCA AAA CTA AAT TCA ACA AAC TTC CCA GAA TTG GAT<br>Tyr Cys Leu Gln Pro Lys Leu Asn Ser Thr Asn Phe Pro Glu Leu Asp<br>70                     75                       80                     85 | 833 |
| GAT GTA GGA TAT TCC ACT GTC ATT TCA TCT ATT CCA CAA TGG ACC AAT<br>Asp Val Gly Tyr Ser Thr Val Ile Ser Ser Ile Pro Gln Trp Thr Asn<br>               90                       95                    100 | 881 |
| CTA CAG TTC TCA TTA GTG AAT GAT TCT AAG TGG TTC AAT CCA CAA AAT<br>Leu Gln Phe Ser Leu Val Asn Asp Ser Lys Trp Phe Asn Pro Gln Asn<br>               105                    110                  115 | 929 |
| GTT ACG TTG GAT GAC GTA ACT AAT TAT AGC CAA AAC TTA TCA ATG AAG<br>Val Thr Leu Asp Asp Val Thr Asn Tyr Ser Gln Asn Leu Ser Met Lys<br>         120                       125                    130 | 977 |
| GAT GGT ATC GTA ACT ACG GAG TTA GAT TGG CTA AAC AGT CAA ATA CAT<br>Asp Gly Ile Val Thr Thr Glu Leu Asp Trp Leu Asn Ser Gln Ile His<br>135                          140                    145 | 1025 |
| GTT AAA AGT GAA ATC TGG GCA CAT CGG CAC ATT CAT CCA CTG GGA GTG<br>Val Lys Ser Glu Ile Trp Ala His Arg His Ile His Pro Leu Gly Val<br>150                     155                    160                  165 | 1073 |
| GTT TCT TTG GAA ATT TCC CTG AAT ACG GAC CAT TTA CCT TCG GAT TTT<br>Val Ser Leu Glu Ile Ser Leu Asn Thr Asp His Leu Pro Ser Asp Phe<br>                    170                      175                  180 | 1121 |
| GAT TCA TTA GAT GTT AAT ATA TGG GAT ATA CTT GAT TTC AAC ACA TCA<br>Asp Ser Leu Asp Val Asn Ile Trp Asp Ile Leu Asp Phe Asn Thr Ser<br>         185                       190                    195 | 1169 |
| CAT AGG ACT GTT CTA CAT AGC ACG GGA ACA GAC GAA AAA AAT AAT GCG<br>His Arg Thr Val Leu His Ser Thr Gly Thr Asp Glu Lys Asn Asn Ala<br>             200                      205                    210 | 1217 |
| GTT TTC ATG ATT GTT CAG CCA GAT AAC GTT CCA TCT TCT AAT TGC GCT<br>Val Phe Met Ile Val Gln Pro Asp Asn Val Pro Ser Ser Asn Cys Ala<br>         215                       220                    225 | 1265 |
| ATT TAC TCA ACG TGT ACT GTA AAG TAT GAA AAT TCC ACC AAT CCA ATA<br>Ile Tyr Ser Thr Cys Thr Val Lys Tyr Glu Asn Ser Thr Asn Pro Ile<br>230                          235                    240                    245 | 1313 |

| | | | | | | | | | | | | | | | | |
|---|---|---|---|---|---|---|---|---|---|---|---|---|---|---|---|---|
| AAT | TCT | AGT | GAA | TCT | TTT | GAA | GAA | AAA | GAT | GTT | TCT | TCT | AAT | ATT | TAT | 1361 |
| Asn | Ser | Ser | Glu | Ser | Phe | Glu | Glu | Lys | Asp | Val | Ser | Ser | Asn | Ile | Tyr | |
| | | | | 250 | | | | 255 | | | | | | 260 | | |
| AAT | GTT | ATT | TTG | AGA | GAG | GAC | CAA | CCC | AAG | ATA | ATC | GTT | CAT | AAG | TAT | 1409 |
| Asn | Val | Ile | Leu | Arg | Glu | Asp | Gln | Pro | Lys | Ile | Ile | Val | His | Lys | Tyr | |
| | | | 265 | | | | | 270 | | | | | 275 | | | |
| GTT | GGT | ATT | ATG | TCT | ACT | GAG | TTC | AAT | AAG | AAC | AAA | GAA | CAA | CAA | GAC | 1457 |
| Val | Gly | Ile | Met | Ser | Thr | Glu | Phe | Asn | Lys | Asn | Lys | Glu | Gln | Gln | Asp | |
| | | | 280 | | | | | 285 | | | | | 290 | | | |
| AAT | ACT | AAT | ATT | GGT | TTG | GCC | AAA | ATG | ATA | GCT | CTA | AAC | AGT | AAA | GGC | 1505 |
| Asn | Thr | Asn | Ile | Gly | Leu | Ala | Lys | Met | Ile | Ala | Leu | Asn | Ser | Lys | Gly | |
| | 295 | | | | 300 | | | | | 305 | | | | | | |
| AAT | TAC | GAG | AAG | CTT | CTG | TCA | AGT | CAC | AAA | CGT | GCG | TGG | TAT | GAC | CTT | 1553 |
| Asn | Tyr | Glu | Lys | Leu | Leu | Ser | Ser | His | Lys | Arg | Ala | Trp | Tyr | Asp | Leu | |
| 310 | | | | | 315 | | | | | 320 | | | | | 325 | |
| TAC | AAC | GAC | GCC | TTC | ATT | GAA | ATT | CCT | TCT | GAC | AGT | CTT | TTA | GAA | ATG | 1601 |
| Tyr | Asn | Asp | Ala | Phe | Ile | Glu | Ile | Pro | Ser | Asp | Ser | Leu | Leu | Glu | Met | |
| | | | | 330 | | | | 335 | | | | | 340 | | | |
| ACA | GCA | AGA | TCG | TCC | CTA | TTC | CAT | TTA | CTA | GCA | AAT | ACA | AGA | GAT | TAC | 1649 |
| Thr | Ala | Arg | Ser | Ser | Leu | Phe | His | Leu | Leu | Ala | Asn | Thr | Arg | Asp | Tyr | |
| | | | 345 | | | | | 350 | | | | | 355 | | | |
| AAT | GTC | TCG | AGC | GAT | AGG | GGT | CTT | CCC | GTG | GGA | GTT | TCT | GGT | TTG | TCA | 1697 |
| Asn | Val | Ser | Ser | Asp | Arg | Gly | Leu | Pro | Val | Gly | Val | Ser | Gly | Leu | Ser | |
| | | | 360 | | | | | 365 | | | | | 370 | | | |
| TCA | GAT | TCC | TAT | GGT | GGT | ATG | GTG | TTC | TGG | GAC | GCA | GAT | ATA | TGG | ATG | 1745 |
| Ser | Asp | Ser | Tyr | Gly | Gly | Met | Val | Phe | Trp | Asp | Ala | Asp | Ile | Trp | Met | |
| | 375 | | | | | 380 | | | | | 385 | | | | | |
| GAA | CCT | GCC | CTA | TTG | CCT | TTC | TTC | CCA | AAT | GTG | GCT | CAA | AAT | ATG | AAT | 1793 |
| Glu | Pro | Ala | Leu | Leu | Pro | Phe | Phe | Pro | Asn | Val | Ala | Gln | Asn | Met | Asn | |
| 390 | | | | | 395 | | | | 400 | | | | | | 405 | |
| AAT | TAC | AGA | AAT | GCT | ACA | CAT | TCG | CAG | GCA | AAG | TTA | AAT | GCA | GAG | AAA | 1841 |
| Asn | Tyr | Arg | Asn | Ala | Thr | His | Ser | Gln | Ala | Lys | Leu | Asn | Ala | Glu | Lys | |
| | | | | 410 | | | | 415 | | | | | 420 | | | |
| TAT | GGA | TAC | CCC | GGA | GCA | ATA | TAC | CCC | TGG | ACA | TCT | GGT | AAG | TAC | GCT | 1889 |
| Tyr | Gly | Tyr | Pro | Gly | Ala | Ile | Tyr | Pro | Trp | Thr | Ser | Gly | Lys | Tyr | Ala | |
| | | | 425 | | | | | 430 | | | | | 435 | | | |
| AAT | TGT | ACT | TCT | ACG | GGA | CCT | TGT | GTC | GAT | TAC | GAA | TAC | CAT | ATT | AAC | 1937 |
| Asn | Cys | Thr | Ser | Thr | Gly | Pro | Cys | Val | Asp | Tyr | Glu | Tyr | His | Ile | Asn | |
| | | | 440 | | | | | 445 | | | | | 450 | | | |
| GTT | GAT | GTC | GCT | ATG | GCC | TCC | TTT | TCC | ATA | TAC | TTG | AAT | GGA | CAC | GAA | 1985 |
| Val | Asp | Val | Ala | Met | Ala | Ser | Phe | Ser | Ile | Tyr | Leu | Asn | Gly | His | Glu | |
| | 455 | | | | | 460 | | | | | 465 | | | | | |
| GGG | ATT | GAT | GAC | GAG | TAT | CTG | AGA | TAT | ACT | ACA | TGG | CCA | ATT | ATC | AAA | 2033 |
| Gly | Ile | Asp | Asp | Glu | Tyr | Leu | Arg | Tyr | Thr | Thr | Trp | Pro | Ile | Ile | Lys | |
| 470 | | | | | 475 | | | | 480 | | | | | | 485 | |
| AAC | GCA | GCC | CAA | TTT | TTT | ACT | GCT | TAT | GTT | AAG | TAC | AAT | TCT | TCC | CTA | 2081 |
| Asn | Ala | Ala | Gln | Phe | Phe | Thr | Ala | Tyr | Val | Lys | Tyr | Asn | Ser | Ser | Leu | |
| | | | | 490 | | | | 495 | | | | | 500 | | | |
| GGA | TTG | TAT | GAA | ACA | TAT | AAT | TTG | ACA | GAT | CCC | GAC | GAG | TTT | GCT | AAT | 2129 |
| Gly | Leu | Tyr | Glu | Thr | Tyr | Asn | Leu | Thr | Asp | Pro | Asp | Glu | Phe | Ala | Asn | |
| | | | 505 | | | | | 510 | | | | | 515 | | | |
| CAC | ATC | AAT | AAC | GGG | GCT | TTC | ACG | AAT | GCT | GGC | ATT | AAA | ACA | CTT | CTA | 2177 |
| His | Ile | Asn | Asn | Gly | Ala | Phe | Thr | Asn | Ala | Gly | Ile | Lys | Thr | Leu | Leu | |
| | | | 520 | | | | | 525 | | | | | 530 | | | |
| AAG | TGG | GCA | ACA | GAC | ATT | GGC | AAT | CAT | CTC | GGC | GAG | GTC | GTT | GAC | CCC | 2225 |
| Lys | Trp | Ala | Thr | Asp | Ile | Gly | Asn | His | Leu | Gly | Glu | Val | Val | Asp | Pro | |
| | | 535 | | | | | 540 | | | | | 545 | | | | |
| AAA | TGG | AGT | GAA | ATT | TCC | AAA | GAT | ATT | TAT | ATC | CCT | AGA | TCC | TCA | TCT | 2273 |
| Lys | Trp | Ser | Glu | Ile | Ser | Lys | Asp | Ile | Tyr | Ile | Pro | Arg | Ser | Ser | Ser | |
| 550 | | | | | 555 | | | | 560 | | | | | | 565 | |

-continued

| | | | | | | | | | | | | | | | | |
|---|---|---|---|---|---|---|---|---|---|---|---|---|---|---|---|---|
| AAC | ATC | ACT | TTG | GAA | TAT | TCT | GGT | ATG | AAT | AGC | TCA | GTG | GAG | ATT | AAA | 2321 |
| Asn | Ile | Thr | Leu | Glu 570 | Tyr | Ser | Gly | Met 575 | Asn | Ser | Ser | Val | Glu | Ile 580 | Lys | |
| CAG | GCG | GAT | GTG | ACT | TTA | ATG | GTT | TAC | CCA | CTT | GGA | TAT | ATC | AAT | GAT | 2369 |
| Gln | Ala | Asp | Val 585 | Thr | Leu | Met | Val | Tyr 590 | Pro | Leu | Gly | Tyr | Ile 595 | Asn | Asp | |
| GAA | TCC | ATA | TTG | AAC | AAT | GCA | ATT | AAA | GAT | CTT | TAT | TAT | TAT | TCA | GAA | 2417 |
| Glu | Ser | Ile 600 | Leu | Asn | Asn | Ala | Ile 605 | Lys | Asp | Leu | Tyr | Tyr 610 | Tyr | Ser | Glu | |
| AGA | CAG | TCT | GCG | TCT | GGG | CCT | GCA | ATG | ACA | TAT | CCG | GTT | TTT | GTG | GCC | 2465 |
| Arg | Gln 615 | Ser | Ala | Ser | Gly | Pro 620 | Ala | Met | Thr | Tyr | Pro 625 | Val | Phe | Val | Ala | |
| GCA | GCT | GCT | GGT | CTG | CTG | AAT | CAC | GGC | TCT | TCT | TCT | CAA | AGT | TAC | TTA | 2513 |
| Ala 630 | Ala | Ala | Gly | Leu | Leu 635 | Asn | His | Gly | Ser | Ser 640 | Ser | Gln | Ser | Tyr | Leu 645 | |
| TAT | AAA | TCG | GTT | CTT | CCA | TAC | TTA | CGG | GCT | CCT | TTC | GCT | CAA | TTT | AGT | 2561 |
| Tyr | Lys | Ser | Val | Leu 650 | Pro | Tyr | Leu | Arg | Ala 655 | Pro | Phe | Ala | Gln | Phe 660 | Ser | |
| GAG | CAA | TCA | GAC | GAC | AAC | TTT | TTA | ACA | AAC | GGA | TTA | ACC | CAG | CCA | GCA | 2609 |
| Glu | Gln | Ser | Asp 665 | Asp | Asn | Phe | Leu | Thr 670 | Asn | Gly | Leu | Thr | Gln 675 | Pro | Ala | |
| TTC | CCC | TTT | TTA | ACA | GCT | AAC | GGT | GGA | TTT | CTA | CAG | AGC | ATT | CTG | TTT | 2657 |
| Phe | Pro | Phe 680 | Leu | Thr | Ala | Asn | Gly 685 | Gly | Phe | Leu | Gln | Ser 690 | Ile | Leu | Phe | |
| GGG | TTA | ACA | GGA | ATC | CGA | TAT | TCT | TAT | GAG | GTT | GAT | CCA | GAT | ACT | AAA | 2705 |
| Gly | Leu | Thr 695 | Gly | Ile | Arg | Tyr | Ser 700 | Tyr | Glu | Val | Asp | Pro 705 | Asp | Thr | Lys | |
| AAA | ATT | AAC | CGT | TTG | TTA | AGG | TTC | AAT | CCA | ATA | GAA | CTA | CCG | TTG | CTC | 2753 |
| Lys 710 | Ile | Asn | Arg | Leu | Leu 715 | Arg | Phe | Asn | Pro | Ile 720 | Glu | Leu | Pro | Leu | Leu 725 | |
| CCT | GGT | GGT | ATC | GCT | ATT | AGA | AAC | TTC | AAA | TAT | ATG | AAC | CCA | GTT | TTA | 2801 |
| Pro | Gly | Gly | Ile | Ala 730 | Ile | Arg | Asn | Phe | Lys 735 | Tyr | Met | Asn | Pro | Val 740 | Leu | |
| GAT | ATA | ATA | ATT | GAC | GAC | CAC | AAT | GGT | ACG | ATT | GTT | CAT | AAA | TCA | GGA | 2849 |
| Asp | Ile | Ile | Ile 745 | Asp | Asp | His | Asn | Gly 750 | Thr | Ile | Val | His | Lys 755 | Ser | Gly | |
| GAT | GTT | CCT | ATT | CAT | ATA | AAG | ATA | CCA | AAC | AGA | TCT | CTA | ATA | CAT | GAC | 2897 |
| Asp | Val | Pro 760 | Ile | His | Ile | Lys | Ile 765 | Pro | Asn | Arg | Ser | Leu 770 | Ile | His | Asp | |
| CAG | GAT | ATC | AAC | TTC | TAT | AAT | GGT | TCC | GAA | AAC | GAA | AGA | AAA | CCA | AAT | 2945 |
| Gln | Asp | Ile 775 | Asn | Phe | Tyr | Asn 780 | Gly | Ser | Glu | Asn | Glu 785 | Arg | Lys | Pro | Asn | |
| CTA | GAG | CGT | AGA | GAC | GTC | GAC | CGT | GTT | GGT | GAT | CCA | ATG | AGG | ATG | GAT | 2993 |
| Leu 790 | Glu | Arg | Arg | Asp | Val 795 | Asp | Arg | Val | Gly | Asp 800 | Pro | Met | Arg | Met | Asp 805 | |
| AGG | TAT | GGT | ACC | TAT | TAT | CTT | TTA | AAA | CCG | AAA | CAA | GAG | CTT | ACA | GTC | 3041 |
| Arg | Tyr | Gly | Thr | Tyr 810 | Tyr | Leu | Leu | Lys | Pro 815 | Lys | Gln | Glu | Leu | Thr 820 | Val | |
| CAA | CTG | TTC | AAG | CCT | GGC | TTA | AAC | GCA | AGA | AAC | AAC | ATA | GCG | GAA | AAT | 3089 |
| Gln | Leu | Phe | Lys 825 | Pro | Gly | Leu | Asn | Ala 830 | Arg | Asn | Asn | Ile | Ala 835 | Glu | Asn | |
| AAG | CAA | ATA | ACA | AAC | TTG | ACG | GCC | GGC | GTT | CCT | GGT | GAC | GTT | GCA | TTC | 3137 |
| Lys | Gln | Ile 840 | Thr | Asn | Leu | Thr | Ala 845 | Gly | Val | Pro | Gly | Asp 850 | Val | Ala | Phe | |
| TCT | GCT | CTA | GAT | GGG | AAT | AAT | TAC | ACG | CAT | TGG | CAA | CCC | TTA | GAC | AAA | 3185 |
| Ser | Ala | Leu 855 | Asp | Gly | Asn | Asn | Tyr 860 | Thr | His | Trp | Gln | Pro 865 | Leu | Asp | Lys | |
| ATT | CAC | CGT | GCG | AAG | CTA | TTG | ATT | GAT | TTA | GGT | GAA | TAC | AAC | GAG | AAA | 3233 |
| Ile | His | Arg | Ala | Lys 875 | Leu | Leu | Ile | Asp | Leu 880 | Gly | Glu | Tyr | Asn | Glu 885 | Lys | |

| | | | | | | | | | | | | | | | | |
|---|---|---|---|---|---|---|---|---|---|---|---|---|---|---|---|---|
| GAG | ATT | ACC | AAG | GGA | ATG | ATT | CTT | TGG | GGG | CAG | AGG | CCC | GCA | AAA | AAC | 3281 |
| Glu | Ile | Thr | Lys | Gly | Met | Ile | Leu | Trp | Gly | Gln | Arg | Pro | Ala | Lys | Asn | |
| | | | 890 | | | | | 895 | | | | | 900 | | | |
| ATT | TCC | ATA | TCT | ATT | TTG | CCT | CAT | TCT | GAA | AAA | GTC | GAA | AAT | TTA | TTT | 3329 |
| Ile | Ser | Ile | Ser | Ile | Leu | Pro | His | Ser | Glu | Lys | Val | Glu | Asn | Leu | Phe | |
| | | | 905 | | | | | 910 | | | | | 915 | | | |
| GCG | AAC | GTG | ACA | GAA | ATT | ATG | CAA | AAT | TCG | GGA | AAT | GAT | CAA | CTT | CTT | 3377 |
| Ala | Asn | Val | Thr | Glu | Ile | Met | Gln | Asn | Ser | Gly | Asn | Asp | Gln | Leu | Leu | |
| | | 920 | | | | | 925 | | | | | 930 | | | | |
| AAT | GAA | ACC | ATT | GGT | CAG | CTT | TTA | GAT | AAT | GCC | GGA | ATT | CCT | GTC | GAG | 3425 |
| Asn | Glu | Thr | Ile | Gly | Gln | Leu | Leu | Asp | Asn | Ala | Gly | Ile | Pro | Val | Glu | |
| | 935 | | | | | 940 | | | | | 945 | | | | | |
| AAC | GTT | ATT | GAT | TTT | GAT | GGC | ATA | GAA | CAA | GAG | GAT | GAT | GAA | TCT | TTG | 3473 |
| Asn | Val | Ile | Asp | Phe | Asp | Gly | Ile | Glu | Gln | Glu | Asp | Asp | Glu | Ser | Leu | |
| 950 | | | | | 955 | | | | | 960 | | | | | 965 | |
| GAT | GAT | GTG | CAA | GCC | TTA | TTG | CAC | TGG | AAG | AAG | GAA | GAC | TTA | GCC | AAG | 3521 |
| Asp | Asp | Val | Gln | Ala | Leu | Leu | His | Trp | Lys | Lys | Glu | Asp | Leu | Ala | Lys | |
| | | | | 970 | | | | | 975 | | | | | 980 | | |
| CTA | ATT | GAC | CAA | ATA | CCC | AGA | CTT | AAC | TTT | CTA | AAA | AGA | AAA | TTT | GTG | 3569 |
| Leu | Ile | Asp | Gln | Ile | Pro | Arg | Leu | Asn | Phe | Leu | Lys | Arg | Lys | Phe | Val | |
| | | | 985 | | | | | 990 | | | | | 995 | | | |
| AAA | ATT | CTG | GAT | AAC | GTG | CCA | GTG | AGC | CCA | AGT | GAG | CCA | TAC | TAC | GAA | 3617 |
| Lys | Ile | Leu | Asp | Asn | Val | Pro | Val | Ser | Pro | Ser | Glu | Pro | Tyr | Tyr | Glu | |
| | | 1000 | | | | | 1005 | | | | | 1010 | | | | |
| GCA | AGT | CGC | AAC | CAG | TCG | TTA | ATC | GAG | ATA | TTA | CCC | AGT | AAT | AGA | ACG | 3665 |
| Ala | Ser | Arg | Asn | Gln | Ser | Leu | Ile | Glu | Ile | Leu | Pro | Ser | Asn | Arg | Thr | |
| | 1015 | | | | | 1020 | | | | | 1025 | | | | | |
| ACT | TTC | ACT | ATT | GAT | TAT | GAT | AAA | TTT | GCA | GGT | GGG | TGATAAAGGG | | | | 3711 |
| Thr | Phe | Thr | Ile | Asp | Tyr | Asp | Lys | Phe | Ala | Gly | Gly | | | | | |
| 1030 | | | | | 1035 | | | | | 1040 | | | | | | |

AACACAGATT GGAGGAAAAC AAGATACATA GTTGTTTCGT ACAAGGAGTG TATGATGATT 3771

ATATGATGAT AACAAGGAG CTACAATCAA GGAAATTGTT CTCAATGATT AAATGAAATG 3831

ATGCATATTA GTAGCGCTTT TTTTAATATT ATAAGTTTGG ATAAA 3876

( 2 ) INFORMATION FOR SEQ ID NO:2:

( i ) SEQUENCE CHARACTERISTICS:
        ( A ) LENGTH: 1041 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Ile | Leu | Gly | Ser | Asn | Leu | Phe | Ser | Lys | Asn | Thr | Tyr | Ser | Arg | Gln |
| 1 | | | | 5 | | | | | 10 | | | | | 15 | |
| Pro | Tyr | Val | Ala | Asn | Gly | Tyr | Ile | Gly | Ser | Arg | Ile | Pro | Asn | Ile | Gly |
| | | | 20 | | | | | 25 | | | | | 30 | | |
| Phe | Gly | Tyr | Ala | Leu | Asp | Thr | Leu | Asn | Phe | Tyr | Thr | Asp | Ala | Pro | Gly |
| | | | 35 | | | | 40 | | | | | 45 | | | |
| Ala | Leu | Asn | Asn | Gly | Trp | Pro | Leu | Arg | Asn | His | Arg | Phe | Ala | Gly | Ala |
| | | 50 | | | | 55 | | | | 60 | | | | | |
| Phe | Val | Ser | Asp | Phe | Tyr | Cys | Leu | Gln | Pro | Lys | Leu | Asn | Ser | Thr | Asn |
| 65 | | | | | 70 | | | | 75 | | | | | | 80 |
| Phe | Pro | Glu | Leu | Asp | Asp | Val | Gly | Tyr | Ser | Thr | Val | Ile | Ser | Ser | Ile |
| | | | | 85 | | | | 90 | | | | | 95 | | |
| Pro | Gln | Trp | Thr | Asn | Leu | Gln | Phe | Ser | Leu | Val | Asn | Asp | Ser | Lys | Trp |
| | | | 100 | | | | 105 | | | | | 110 | | | |
| Phe | Asn | Pro | Gln | Asn | Val | Thr | Leu | Asp | Asp | Val | Thr | Asn | Tyr | Ser | Gln |

|     |     |     | 115 |     |     |     | 120 |     |     |     | 125 |     |     |     |
| --- | --- | --- | --- | --- | --- | --- | --- | --- | --- | --- | --- | --- | --- | --- |
| Asn | Leu | Ser | Met | Lys | Asp | Gly | Ile | Val | Thr | Thr | Glu | Leu | Asp | Trp | Leu |
|     | 130 |     |     |     |     | 135 |     |     |     |     | 140 |     |     |     |     |
| Asn | Ser | Gln | Ile | His | Val | Lys | Ser | Glu | Ile | Trp | Ala | His | Arg | His | Ile |
| 145 |     |     |     |     | 150 |     |     |     |     | 155 |     |     |     |     | 160 |
| His | Pro | Leu | Gly | Val | Val | Ser | Leu | Glu | Ile | Ser | Leu | Asn | Thr | Asp | His |
|     |     |     |     |     | 165 |     |     |     |     | 170 |     |     |     |     | 175 |
| Leu | Pro | Ser | Asp | Phe | Asp | Ser | Leu | Asp | Val | Asn | Ile | Trp | Asp | Ile | Leu |
|     |     |     | 180 |     |     |     |     | 185 |     |     |     |     | 190 |     |     |
| Asp | Phe | Asn | Thr | Ser | His | Arg | Thr | Val | Leu | His | Ser | Thr | Gly | Thr | Asp |
|     |     | 195 |     |     |     |     | 200 |     |     |     |     | 205 |     |     |     |
| Glu | Lys | Asn | Asn | Ala | Val | Phe | Met | Ile | Val | Gln | Pro | Asp | Asn | Val | Pro |
|     | 210 |     |     |     |     | 215 |     |     |     |     | 220 |     |     |     |     |
| Ser | Ser | Asn | Cys | Ala | Ile | Tyr | Ser | Thr | Cys | Thr | Val | Lys | Tyr | Glu | Asn |
| 225 |     |     |     |     | 230 |     |     |     |     | 235 |     |     |     |     | 240 |
| Ser | Thr | Asn | Pro | Ile | Asn | Ser | Ser | Glu | Ser | Phe | Glu | Glu | Lys | Asp | Val |
|     |     |     |     | 245 |     |     |     |     | 250 |     |     |     |     | 255 |     |
| Ser | Ser | Asn | Ile | Tyr | Asn | Val | Ile | Leu | Arg | Glu | Asp | Gln | Pro | Lys | Ile |
|     |     |     | 260 |     |     |     |     | 265 |     |     |     |     | 270 |     |     |
| Ile | Val | His | Lys | Tyr | Val | Gly | Ile | Met | Ser | Thr | Glu | Phe | Asn | Lys | Asn |
|     |     | 275 |     |     |     |     | 280 |     |     |     |     | 285 |     |     |     |
| Lys | Glu | Gln | Gln | Asp | Asn | Thr | Asn | Ile | Gly | Leu | Ala | Lys | Met | Ile | Ala |
|     | 290 |     |     |     |     | 295 |     |     |     |     | 300 |     |     |     |     |
| Leu | Asn | Ser | Lys | Gly | Asn | Tyr | Glu | Lys | Leu | Leu | Ser | Ser | His | Lys | Arg |
| 305 |     |     |     |     | 310 |     |     |     |     | 315 |     |     |     |     | 320 |
| Ala | Trp | Tyr | Asp | Leu | Tyr | Asn | Asp | Ala | Phe | Ile | Glu | Ile | Pro | Ser | Asp |
|     |     |     |     | 325 |     |     |     |     | 330 |     |     |     |     | 335 |     |
| Ser | Leu | Leu | Glu | Met | Thr | Ala | Arg | Ser | Ser | Leu | Phe | His | Leu | Leu | Ala |
|     |     |     | 340 |     |     |     |     | 345 |     |     |     |     | 350 |     |     |
| Asn | Thr | Arg | Asp | Tyr | Asn | Val | Ser | Ser | Asp | Arg | Gly | Leu | Pro | Val | Gly |
|     |     | 355 |     |     |     |     | 360 |     |     |     |     | 365 |     |     |     |
| Val | Ser | Gly | Leu | Ser | Ser | Asp | Ser | Tyr | Gly | Gly | Met | Val | Phe | Trp | Asp |
|     | 370 |     |     |     |     | 375 |     |     |     |     | 380 |     |     |     |     |
| Ala | Asp | Ile | Trp | Met | Glu | Pro | Ala | Leu | Leu | Pro | Phe | Phe | Pro | Asn | Val |
| 385 |     |     |     |     | 390 |     |     |     |     | 395 |     |     |     |     | 400 |
| Ala | Gln | Asn | Met | Asn | Asn | Tyr | Arg | Asn | Ala | Thr | His | Ser | Gln | Ala | Lys |
|     |     |     |     | 405 |     |     |     |     | 410 |     |     |     |     | 415 |     |
| Leu | Asn | Ala | Glu | Lys | Tyr | Gly | Tyr | Pro | Gly | Ala | Ile | Tyr | Pro | Trp | Thr |
|     |     |     | 420 |     |     |     |     | 425 |     |     |     |     | 430 |     |     |
| Ser | Gly | Lys | Tyr | Ala | Asn | Cys | Thr | Ser | Thr | Gly | Pro | Cys | Val | Asp | Tyr |
|     |     | 435 |     |     |     |     | 440 |     |     |     |     | 445 |     |     |     |
| Glu | Tyr | His | Ile | Asn | Val | Asp | Val | Ala | Met | Ala | Ser | Phe | Ser | Ile | Tyr |
|     | 450 |     |     |     |     | 455 |     |     |     |     | 460 |     |     |     |     |
| Leu | Asn | Gly | His | Glu | Gly | Ile | Asp | Asp | Glu | Tyr | Leu | Arg | Tyr | Thr | Thr |
| 465 |     |     |     |     | 470 |     |     |     |     | 475 |     |     |     |     | 480 |
| Trp | Pro | Ile | Ile | Lys | Asn | Ala | Ala | Gln | Phe | Phe | Thr | Ala | Tyr | Val | Lys |
|     |     |     |     | 485 |     |     |     |     | 490 |     |     |     |     | 495 |     |
| Tyr | Asn | Ser | Ser | Leu | Gly | Leu | Tyr | Glu | Thr | Tyr | Asn | Leu | Thr | Asp | Pro |
|     |     |     | 500 |     |     |     |     | 505 |     |     |     |     | 510 |     |     |
| Asp | Glu | Phe | Ala | Asn | His | Ile | Asn | Asn | Gly | Ala | Phe | Thr | Asn | Ala | Gly |
|     |     | 515 |     |     |     |     | 520 |     |     |     |     | 525 |     |     |     |
| Ile | Lys | Thr | Leu | Leu | Lys | Trp | Ala | Thr | Asp | Ile | Gly | Asn | His | Leu | Gly |
|     | 530 |     |     |     |     | 535 |     |     |     |     | 540 |     |     |     |     |

| | | | | | | | | | | | | | | | |
|---|---|---|---|---|---|---|---|---|---|---|---|---|---|---|---|
| Glu 545 | Val | Val | Asp | Pro | Lys 550 | Trp | Ser | Glu | Ile 555 | Ser | Lys | Asp | Ile | Tyr | Ile 560 |
| Pro | Arg | Ser | Ser | Ser 565 | Asn | Ile | Thr | Leu | Glu 570 | Tyr | Ser | Gly | Met | Asn 575 | Ser |
| Ser | Val | Glu | Ile 580 | Lys | Gln | Ala | Asp | Val 585 | Thr | Leu | Met | Val | Tyr 590 | Pro | Leu |
| Gly | Tyr | Ile 595 | Asn | Asp | Glu | Ser | Ile 600 | Leu | Asn | Asn | Ala | Ile 605 | Lys | Asp | Leu |
| Tyr | Tyr 610 | Tyr | Ser | Glu | Arg | Gln 615 | Ser | Ala | Ser | Gly | Pro 620 | Ala | Met | Thr | Tyr |
| Pro 625 | Val | Phe | Val | Ala | Ala 630 | Ala | Ala | Gly | Leu | Leu 635 | Asn | His | Gly | Ser | Ser 640 |
| Ser | Gln | Ser | Tyr | Leu 645 | Tyr | Lys | Ser | Val | Leu 650 | Pro | Tyr | Leu | Arg | Ala 655 | Pro |
| Phe | Ala | Gln | Phe 660 | Ser | Glu | Gln | Ser | Asp 665 | Asp | Asn | Phe | Leu | Thr 670 | Asn | Gly |
| Leu | Thr | Gln 675 | Pro | Ala | Phe | Pro | Phe 680 | Leu | Thr | Ala | Asn | Gly 685 | Gly | Phe | Leu |
| Gln | Ser 690 | Ile | Leu | Phe | Gly | Leu 695 | Thr | Gly | Ile | Arg | Tyr 700 | Ser | Tyr | Glu | Val |
| Asp 705 | Pro | Asp | Thr | Lys | Lys 710 | Ile | Asn | Arg | Leu | Leu 715 | Arg | Phe | Asn | Pro 720 | Ile |
| Glu | Leu | Pro | Leu | Leu 725 | Pro | Gly | Gly | Ile | Ala 730 | Ile | Arg | Asn | Phe | Lys 735 | Tyr |
| Met | Asn | Pro | Val 740 | Leu | Asp | Ile | Ile | Ile 745 | Asp | Asp | His | Asn | Gly 750 | Thr | Ile |
| Val | His | Lys 755 | Ser | Gly | Asp | Val | Pro 760 | Ile | His | Ile | Lys | Ile 765 | Pro | Asn | Arg |
| Ser | Leu 770 | Ile | His | Asp | Gln | Asp 775 | Ile | Asn | Phe | Tyr | Asn 780 | Gly | Ser | Glu | Asn |
| Glu 785 | Arg | Lys | Pro | Asn | Leu 790 | Glu | Arg | Arg | Asp | Val 795 | Asp | Arg | Val | Gly | Asp 800 |
| Pro | Met | Arg | Met | Asp 805 | Arg | Tyr | Gly | Thr | Tyr 810 | Tyr | Leu | Leu | Lys | Pro 815 | Lys |
| Gln | Glu | Leu | Thr 820 | Val | Gln | Leu | Phe | Lys 825 | Pro | Gly | Leu | Asn | Ala 830 | Arg | Asn |
| Asn | Ile | Ala 835 | Glu | Asn | Lys | Gln | Ile 840 | Thr | Asn | Leu | Thr | Ala 845 | Gly | Val | Pro |
| Gly | Asp 850 | Val | Ala | Phe | Ser | Ala 855 | Leu | Asp | Gly | Asn | Asn 860 | Tyr | Thr | His | Trp |
| Gln 865 | Pro | Leu | Asp | Lys | Ile 870 | His | Arg | Ala | Lys | Leu 875 | Leu | Ile | Asp | Leu | Gly 880 |
| Glu | Tyr | Asn | Glu | Lys 885 | Glu | Ile | Thr | Lys | Gly 890 | Met | Ile | Leu | Trp | Gly 895 | Gln |
| Arg | Pro | Ala | Lys 900 | Asn | Ile | Ser | Ile | Ser 905 | Ile | Leu | Pro | His | Ser 910 | Glu | Lys |
| Val | Glu | Asn 915 | Leu | Phe | Ala | Asn | Val 920 | Thr | Glu | Ile | Met | Gln 925 | Asn | Ser | Gly |
| Asn | Asp 930 | Gln | Leu | Leu | Asn | Glu 935 | Thr | Ile | Gly | Gln | Leu 940 | Leu | Asp | Asn | Ala |
| Gly 945 | Ile | Pro | Val | Glu | Asn 950 | Val | Ile | Asp | Phe | Asp 955 | Gly | Ile | Glu | Gln | Glu 960 |
| Asp | Asp | Glu | Ser | Leu 965 | Asp | Asp | Val | Gln | Ala 970 | Leu | Leu | His | Trp | Lys 975 | Lys |

| | | | | | | | | | | | | | | |
|---|---|---|---|---|---|---|---|---|---|---|---|---|---|---|
| Glu | Asp | Leu | Ala 980 | Lys | Leu | Ile | Asp | Gln 985 | Ile | Pro | Arg | Leu | Asn 990 | Phe | Leu |
| Lys | Arg | Lys 995 | Phe | Val | Lys | Ile | Leu 1000 | Asp | Asn | Val | Pro | Val 1005 | Ser | Pro | Ser |
| Glu | Pro 1010 | Tyr | Tyr | Glu | Ala | Ser 1015 | Arg | Asn | Gln | Ser | Leu 1020 | Ile | Glu | Ile | Leu |
| Pro 1025 | Ser | Asn | Arg | Thr | Thr 1030 | Phe | Thr | Ile | Asp | Tyr 1035 | Asp | Lys | Phe | Ala | Gly 1040 |
| Gly | | | | | | | | | | | | | | | |

STRESS TOLERANT YEAST MUTANTS

The research carried out in the subject application was supported in part by grants from the National Institutes of Health. The government may have rights in any patent issuing on this application.

INTRODUCTION

1. Technical Field

The technical field of this invention concerns a specific genetic mutation in yeast which provides enhanced stress tolerance.

2. Background

The non-reducing disaccharide O-α-D-glucopyranosyl-1->1-α-D-glucopyranoside, commonly known as trehalose, was discovered in 1832 (Wiggers, 1832) in a fungus, *Secale cornutum*. Since then, trehalose has been found in a wide variety of organisms including additional fungi, bacteria, plants, insects and other invertebrates. In *Saccharomyces cerevisiae*, trehalose is one of the major storage carbohydrates, accounting for up to 23% or more of the dry weight of the cells, depending on growth conditions and the stage of life cycle (Elbein, 1974).

Trehalose is believed to function in yeast as an energy source in spore germination and as a protecting agent for maintaining structural integrity under environmental stresses such as heat and desiccation (Thevelein, 1984). More recent results, however, indicate that the bulk of trehalose accumulated in yeast under mild heat treatment is not sufficient to account for the acquisition of thermotolerance (Arguelles, 1994; Nwaka et al., 1994; Winkler et al., 1991). The concentration of trehalose in the yeast cell is the result of the activities of the synthesizing bifunctional enzyme trehalose-6-phosphate-synthase/trehalose-6-phosphate phosphatase (Vuorio et al., 1993) and the trehalose hydrolyzing enzymes, e.g. cytosolic neutral trehalase (App and Holzer, 1989) and vacuolar acid trehalase (Mittenbühler and Holzer, 1988). The recently cloned neutral trehalase (NTH) is considered to be the key enzyme responsible for trehalose degradation in intact yeast cells (Kopp et al., 1993; Wiemken, 1990), however, very little is known about the biological function and possible control mechanisms for vacuolar acid trehalase (ATH). ATH has been shown to be glycosylated (Londesborough and Varimo, 1984; Mittenbühler and Holzer, 1988) and activation is dependent on the PEP4 gene product, proteinase A (Harris and Cotter, 1987). The physiological role of ATH and the coordination of its function with that of NTH is unknown.

Due to its role in stress protection, trehalose has important commercial applications for the baking and brewing industries (Mansure et al., 1994; Oda et al., 1986; Hino et al., 1990; Gelinas et al., 1989). The synthesis and degradation of trehalose is important in yeast cell physiology at various stages of growth; mobilization of trehalose and the timing of its metabolism are critical for yeast growth and survival.

SUMMARY OF THE INVENTION

The invention provides methods and compositions relating to stress tolerant yeast; in particular, yeast mutants deficient in the expression of functional ATH1 gene product (Ath1p). An exemplary haploid *S. cerevisiae* strain, identified as MDY3, is deposited at the Section of Microbiology, University of California, Davis.

Such yeast have broad industrial application. For example, in the baking industries, the enhanced tolerance to dehydration and freezing make the mutant yeast particularly suited for use in frozen dough and dehydrated yeast products. In brewing, the mutant yeast strains are able to grow to a higher cell density over a range of fermentable carbon source (e.g. glucose) concentrations and are able to produce and/or tolerate higher levels of ethanol. Accordingly, these strains are used to generate higher ethanol concentrations, take fermentation to a greater degree of completion (to make drier wine) and complete fermentation faster. The subject yeast also find use as an improved source of trehalose (trehalose is used commercially as a protectant in food and pharmaceutical processes) and as a source of ethanol as fuel or additive for spirits: e.g. using inexpensive fermentation substrates such as molasses or corn syrup.

The invention also encompasses isolated nucleic acids comprising ATH1 (SEQUENCE ID NO:1) or fragment thereof capable of hybridizing under stringent conditions with ATH1; and in particular, genetic constructs comprising in 5'-3' orientation, a first ATH1 fragment capable of hybridizing under stringent conditions with ATH1, an intervening sequence, and a second different ATH1 fragment capable of hybridizing under stringent conditions with ATH1.

The invention provides methods for producing a yeast mutant with improved survival ability under stress conditions which involve identifying mutations disrupting ATH1 expression using Ath1-specific reagents or ATH1 hybridization probes or primers.

DESCRIPTION OF SPECIFIC EMBODIMENTS

The subject yeast mutants are specifically deficient in the expression of a functional ATH1 gene product. Such a mutant expresses less than half, preferably less than 25%, more preferably less than 10% and more preferably less than 1% of the functional Ath1p expressed by the corresponding wild-type yeast. A variety of genetic mutations yield mutants deficient in the expression of functional ATH1 gene product; preferred mutants have at least one ATH1 allele rendered nonfunctional (i.e. incapable of generating a functional ATH1 gene product). In one embodiment, the invention provides such mutants wherein said mutant or an ancestor of said mutant was generated by genetically engineering a yeast cell to create a nonfunctional mutation in an Ath1p allele of said yeast cell. A particular exemplary mutant, known herein as MDY3, is on deposit at the University of California, Davis, Section of Microbiology.

Figure 4A:
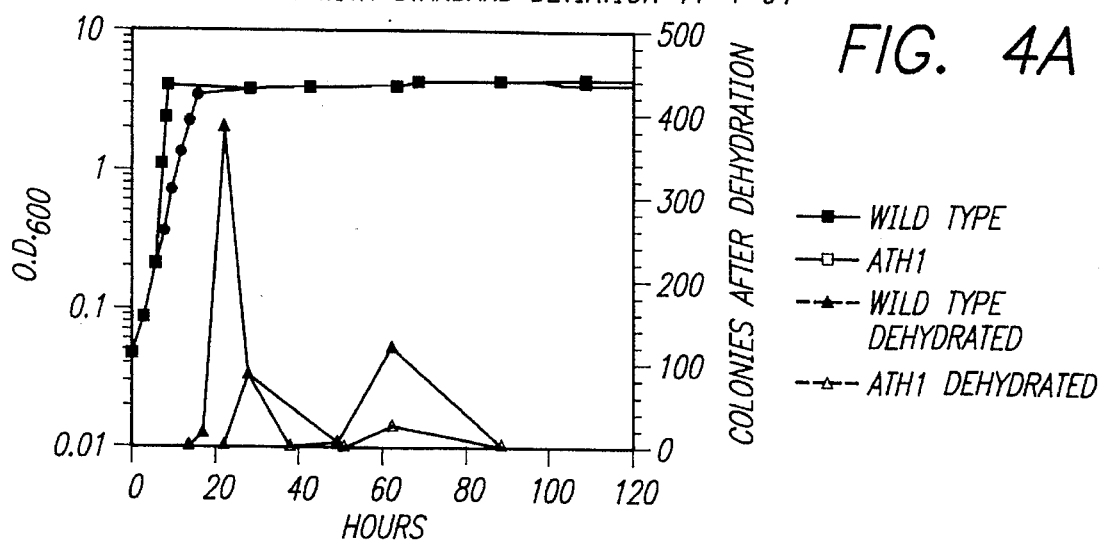
FIG. 4A shows growth versus percent survival over time following dehydration curves.
Figure 4B:
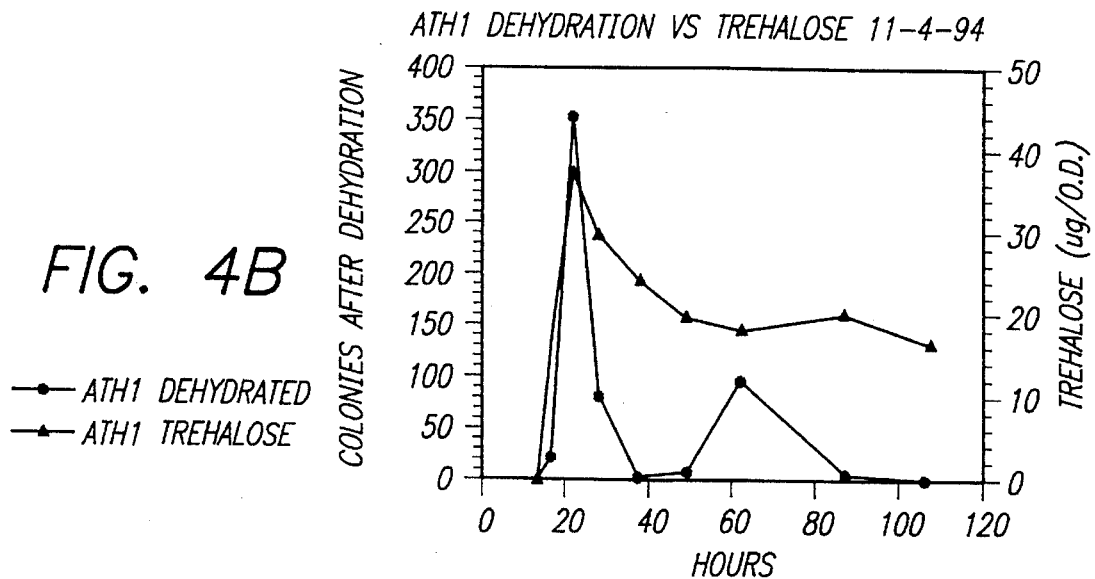
FIG. 4B shows percent survival versus trehalose concentration over time following dehydration curves for ATH1 mutant yeast.
Figure 4C:
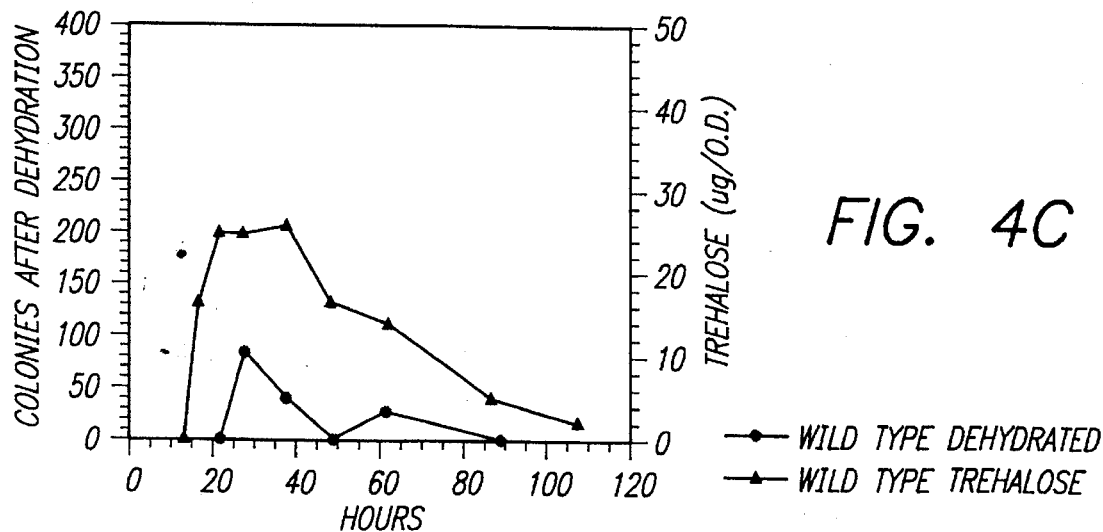
FIG. 4C shows percent survival versus trehalose concentration over time following dehydration curves for wild-type yeast.

Phenotypically, such yeast mutants share a number of characteristics including enhanced survival following dehydration, enhanced ethanol tolerance, and enhanced trehalose production. The post-dehydration survivability enhancement is most apparent as the yeast transit from exponential to stationary growth phases. For cells experiencing dehydration at time points from about 0–10 hours following that transition, and usually from about 1–5 hours following transition, until about 20, often 30, and even 40 or more hours later, the mutant yeast demonstrate a significant enhancement in survivability as compared with the corresponding wild-type yeast. See for example, FIG. 1 and FIG. 4A. This enhanced survivability often correlates with enhanced trehalose concentrations; see, FIGS. 4B and 4C. Mutant survival is generally at least 10%, preferably at least 20%, more preferably at least 50%, more preferably at least 100% (i.e. double) more than the corresponding wild-type yeast during at least one time point.

The subject mutants demonstrate enhanced ethanol tolerance. The mutant yeast are thus able to generate higher ethanol media concentrations than their wild-type counterparts: generally at least 5%, preferably at least 10%, more preferably at least 20% higher ethanol concentration at least one nutrient condition and time point. See for example, FIG. 2. The subject mutants also demonstrate enhanced trehalose concentrations as compared with their wild-type counterparts: generally at least 5%, preferably at least 10%, more preferably at least 20% higher trehalose concentration at least one nutrient condition and time point. See for example, FIG. 3.

The invention provides isolated nucleic acids comprising ATH1 (SEQUENCE ID NO:1) or fragments thereof capable of hybridizing under stringent conditions with ATH1. The subject nucleic acids are either isolated, partially purified, or recombinant. An "isolated" nucleic acid is present as other than a naturally occurring chromosome or transcript in its natural state and isolated from (not joined in sequence to) at least one nucleotide with which it is normally associated on a natural chromosome; a partially pure nucleic acid constitutes at 1.0 least about 5%, preferably at least about 30%, and more preferably at least about 90% by weight of total nucleic acid present in a given fraction; and a recombinant nucleic acid is flanked—joined in sequence on at least one side—by at least one nucleotide with which it is not normally associated on a natural chromosome.

The subject nucleic acids include ATH1 probes and primers comprising one or more ATH1 fragments capable of hybridizing with ATH1 under stringent conditions, e.g. under stringency conditions characterized by a hybridization buffer comprising 0% formamide in 0.9M saline/0.09M sodium citrate (SSC) buffer at a temperature of 37° C. and remaining bound when subject to washing at 42° C. with the SSC buffer at 37° C. Preferred nucleic acids will hybridize in a hybridization buffer comprising 20% formamide in 0.9M saline/0.09M sodium citrate (SSC) buffer at a temperature of 42° C. and remaining bound when subject to washing at 42° C. with 2×SSC buffer at 42° C.

The subject nucleic acids may be introduced into a variety of genetic constructs, plasmids, vectors and cells. For example, a construct useful in generating ATH1 deletion mutants comprises in 5'-3' orientation, a first ATH1 fragment thereof capable of hybridizing under stringent conditions with ATH1, an intervening sequence, and a second different ATH 1 fragment thereof capable of hybridizing under stringent conditions with ATH1.

The invention also provides ATH1 gene products and ATH1 gene product-specific binding agents. ATH1 gene products include ATH 1 translation products such as Ath1p (SEQUENCE ID NO:2). Binding agents specific for such gene products are produced or identified by a variety of ways. For example, Ath1p peptides are used as immunogens to generate specific polyclonal or monoclonal antibodies. See, Harlow and Lane (1988) Antibodies, A Laboratory Manual, Cold Spring Harbor Laboratory, for general methods. Other prospective Ath1p-peptide specific agents are screened from large libraries of synthetic or natural compounds using any convenient binding assay. Such binding agents are capable of binding an ATH1 gene product with an equilibrium constant at least about $10^7 M^{-1}$, preferably at least about $10^8 M^{-1}$, more preferably at least about $10^9 M^{-1}$.

The invention provide methods for producing ATH1 yeast mutants with improved survival ability under stress conditions. In general, the methods involve subjecting a population of yeast to stress conditions, detecting in said population a yeast mutant deficient in the expression of functional Ath1p gene product and growing said yeast mutant to obtain yeast with improved survival ability under stress conditions. The methods may include subjecting the yeast population to conditions promoting mutation, which may be random (e.g. chemical, uv radiation, etc.) or site-directed mutagenesis conditions, of one or more ATH1 alleles and selection for the mutant genotype. The stress conditions provide a selective growth and/or survival advantage for ATH1 mutants deficient in the expression of functional Ath1p gene product (e.g. elevated ethanol media concentration, dehydration, etc.). Targeted mutations are conveniently detected using ATH1 specific oligonucleotide primers or probes, by using Ath1p gene product-specific binding agents (i.e. detecting a deficiency in the expression of functional ATH1 gene product) such as Ath1p specific antibodies, or any other convenient method.

The following examples are offered by way of illustration and not by way of limitation.

EXAMPLES

Figure 1:
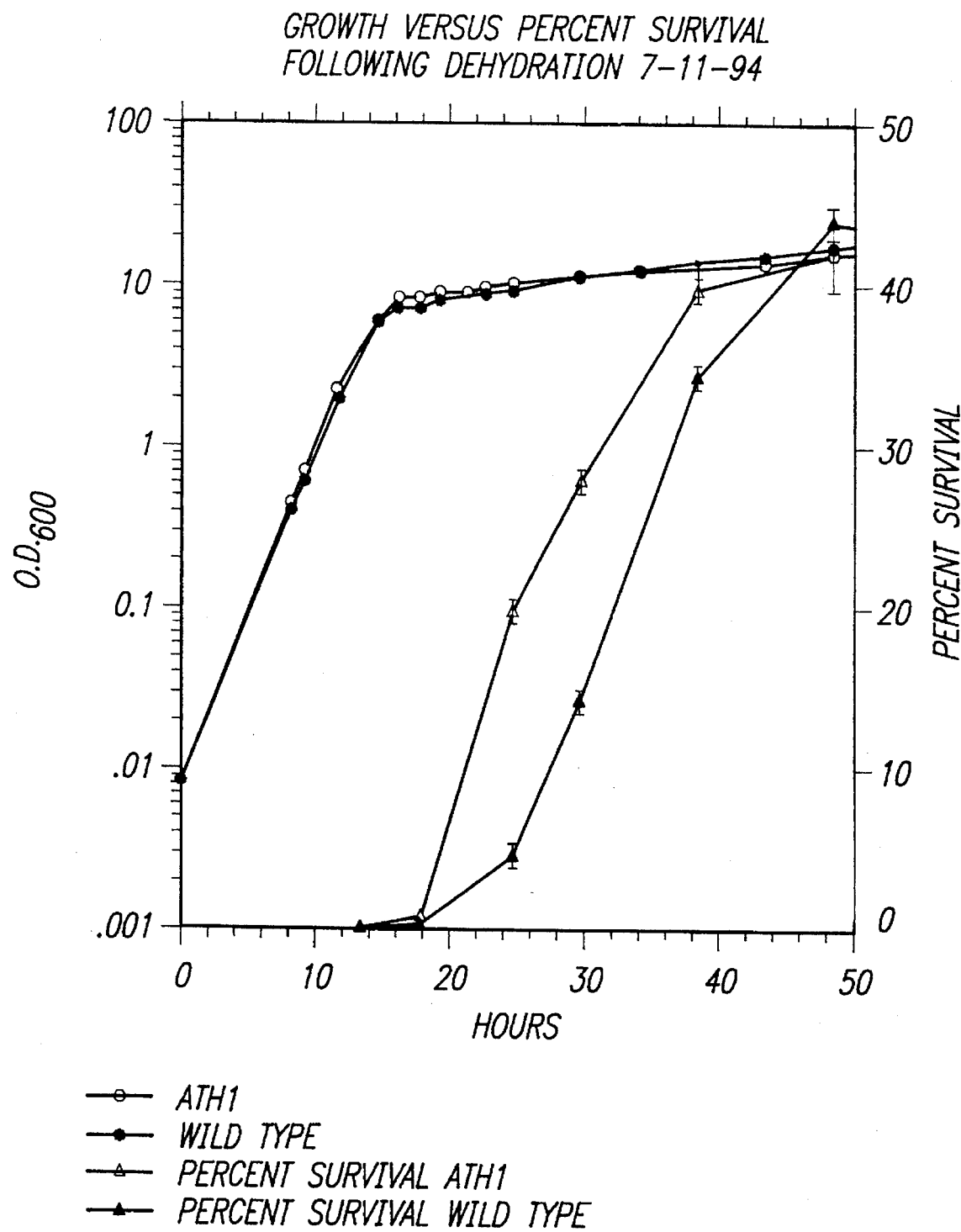
FIG. 1 shows growth versus percent survival over time following dehydration curves.

Protocol for FIG. 1

Examination of effect of Δath1 mutation on survival following dehydration.

1. Grow SEY6210 or SEY6210 Δath1::URA3 in YNBD medium or YNBD medium —URA. Subculture into YPD (2% glucose) and monitor growth.

2. Spin 4×5 O.D.s at 14 hour time point and wash in 50 mM MES pH 5.5. Resuspend in 0.45 ml 50 mM MES pH 5.5.

3. Transfer 0.1 ml to two new microfuge tubes and hold at 24° C.

4. Read O.D.600 of remaining sample (25 ul in 2 ml).

5. Allow one set of samples to dehydrate in speed vac to constant weight (9 hours). Keep at room temperature 8 days. Rehydrate for 10 minutes in 0.5 ml 50 mM MES prewarmed to 40° C.

6. Pellet one set and freeze at −20° C. for determination of carbohydrate.

7. Dilute remaining two samples by adding 400 ul of MES. Freeze one sample by cooling to 4° C.@4° C./min, 2° C.@1° C./min, −20° C.@0.5° C./min and holding at −20° C. for 10 min. Thaw rapidly in water bath at 30° C.

8. Hold remaining sample at room temperature for control and plate during freezing of experimental cells.

9. Dilute cells in 50 mM MES. Plate (50 ul) in triplicate and compare frozen and dehydrated cells to control cells for viability count: Dehydrated: 1:1000K--3; 1:100K--3; 1:10K--3; 1:100--3; 1:10--3; 1:1--3 Frozen, control: 1:1000K--3; 1:100K--3; 1:10K--3

Figure 2:
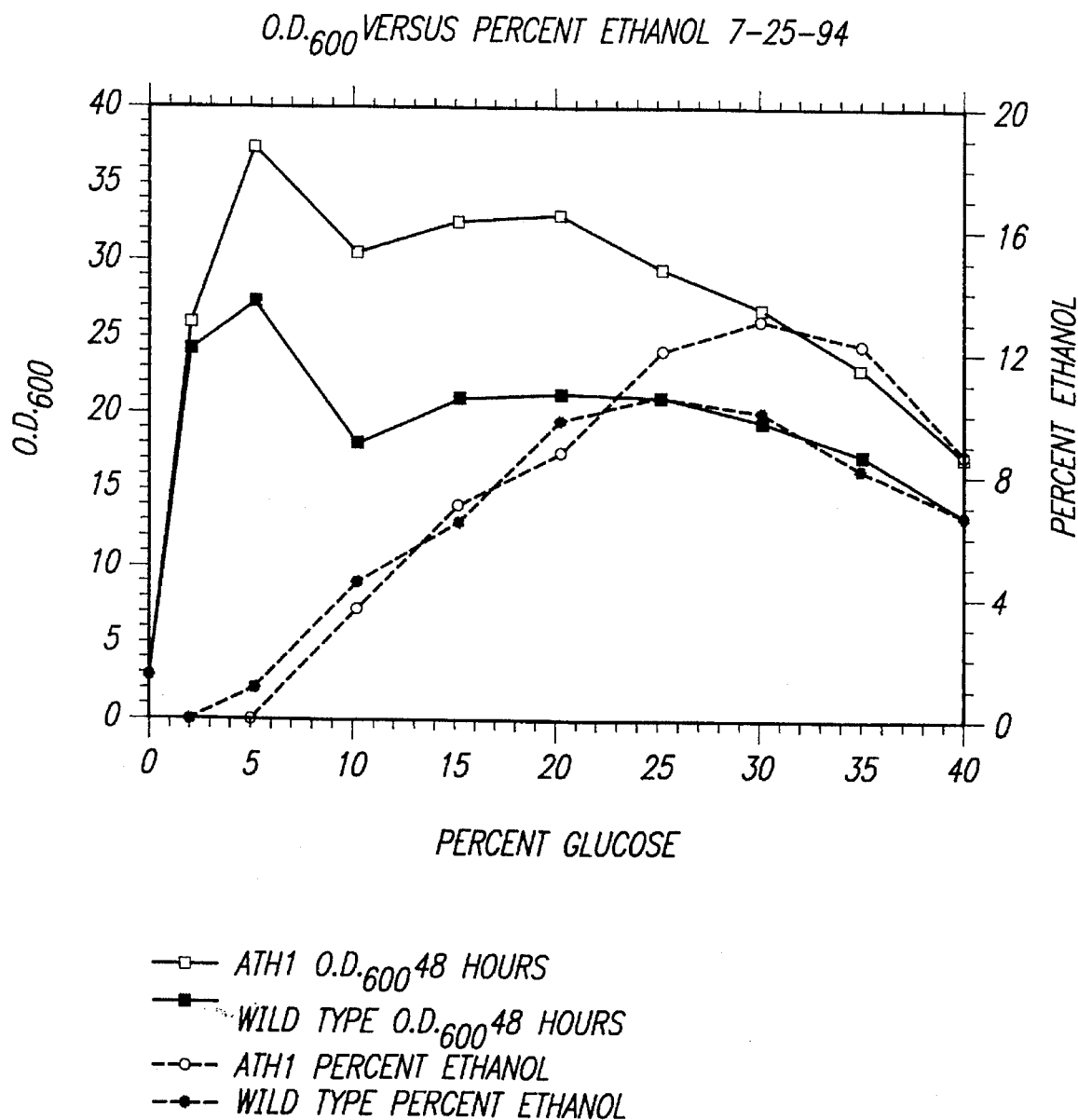
FIG. 2 shows growth versus percent ethanol over glucose concentration curves.
Figure 3:
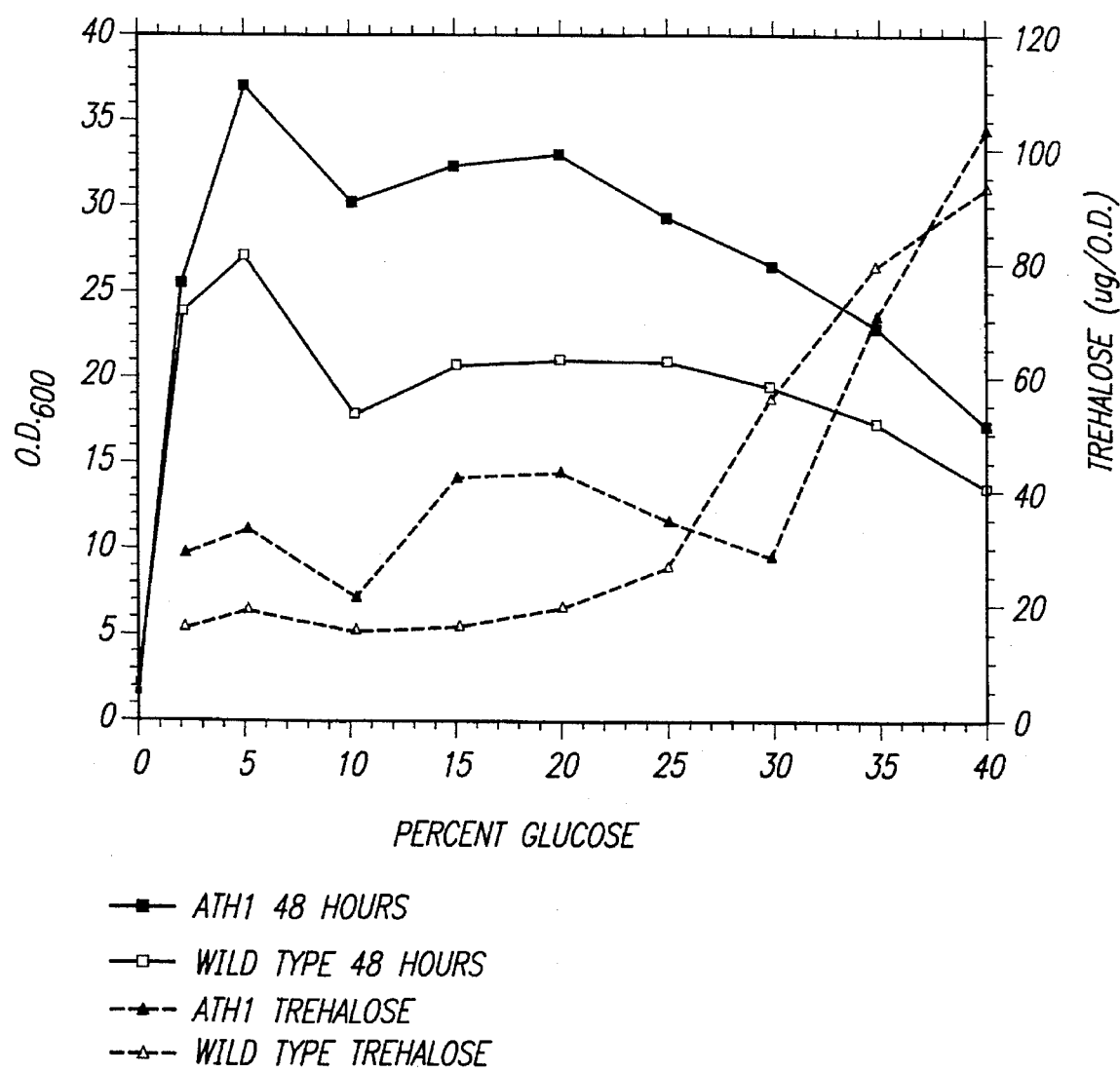
FIG. 3 shows growth versus trehalose concentration over glucose concentration curves.

Protocol for FIGS. 2 and 3

Examine growth of Δath1 strain in varying glucose concentrations.
1. Grow SEY6210 and dath1 in YPD (2%). Subculture and grow to O.D.=3.0.
2. Inoculate YPD (5 ml) having various concentrations of glucose (0–40%). Start cultures at O.D.=0.125.
3. Check O.D. after 24, 48 and 72 hours (50 ul in 2.45 ml).
4. Remove samples for ethanol, glucose and trehalose analysis. Remove 25 O.D.s of cells from each glucose concentration at the 48 hour time point and spin. Remove supernatant (1.0 ml) and freeze for analysis of glucose and ethanol levels. Wash pellet in 1 X YNB and freeze for analysis of trehalose.

Protocol for FIG. 4

Examine effect of Δath1 mutation on survival following drying (growth in minimal medium).
1. Grow SEY6210 or SEY6210 dath1::URA3 in 100 ml YNBD medium (plus URA for both) to respiratory or stationary phase.
2. Spin 4×50.D.s [for trehalose assay: spin an additional 10 O.D.s] and wash in 1 X YNB. Resuspend in 1.5 ml 1 X YNB [for trehalose assay: wash twice, R/S in 100 ul and read O.D. of 5 ul. Freeze remainder].
3. Transfer 0.47 ml to three new microfuge tubes.
4. Read O.D.600 of remaining sample (25 ul in 1 ml).
5. Pellet two sets, remove supernatant and R/S in 120 ul of 1 X YNB. Read O.D.600 of 5 ul. Transfer 100 ul to new tube, weigh and place in speed-vac. Lyophilize until constant weight (3–5 hours). Keep at room temperature for 33 days. Rehydrate one set in 1 X YNB prewarmed to 40° C. (0.47 ml) and plate in dilutions. Other set is a back-up.
6. Hold one set at room temperature for controls and plate during dehydration of experimental cells.
7. Dilute in 1 X YNB. Plate (50 ul) in triplicate and compare dehydrated cells to control cells for viability count.

Strains and media: the *Escherichia coli* strains used in this study were MC1061 F⁻ hsdR⁻ hsdM⁺ araD139 Δ(araABOIC-leu)7679 ΔlacX74 galU galK rpsL (Casadaban and Cohen, 1980) and DH5a F⁻ ø80dlacZΔM15 Δ(lacZYA-argF)U169 deoR recA1 endA1 hsdR17 supE44 1⁻ thi-1 gyrA96 relA1. The yeast strains used were SEY6210 MATa ura3-52 leu2-3,112 his3-Δ200 trpl-Δ901 lys2-801 suc2Δ9 and SEY6211 MATa ura3-52 leu2-3,112 his3-Δ200 trpl-Δ901 ade2-101 suc2Δ9. Standard methods were used to construct yeast strain MDY3 ura3-52 leu2-3,112 his3-Δ200 trpl-Δ901 lys2-801 suc2Δ9 Δath1::URA3. Standard yeast (Sherman et al., 1979; Wickerham, 1946) and *E. coli* media (Miller, 1972) were used and supplemented as needed.

Reagents. YNB, Bacto Tryptone, Bacto Peptone, Bacto Yeast Extract and Bacto Agar were from Difco Laboratories (Detroit, Mich.). DNA restriction and modifying enzymes were from New England Biolabs, Inc. (Beverly, Mass.), and Boehringer Mannheim Biochemicals (Mannheim, Germany). Hybond N⁺ membranes for Southern and Northern (RNA) blots, [a-³²P]dCTP (3,000 Ci/mmol), and [³⁵S]dATPaS (>1,000 Ci/mmol) were from Amersham Buchler (Braunschweig, Germany). Random priming materials and additional enzymes were from United States Biochemical Corp. (Cleveland, Ohio). Biochemical reagents were from Sigma (Deisenhofen, Germany).

Enzymatic overlay assay. Preparation and transformation of competent yeast cells by the lithium-acetate method was carried out as described by Ito (Ito et al., 1983). Yeast colonies transformed with DNA from a genomic plasmid library were replica-plated on YP (1% Bacto Yeast Extract, 2% Bacto Peptone) plates with 2% fructose as the carbohydrate source. After growth for 2 days at 30° C., 10 ml of an overlay-assay-mix that measures secreted ATH activity was poured onto each plate. The assay was performed as described previously (Kopp et al., 1993) with the following modifications: To prepare 100 ml of final volume of the overlay assay mix, 3.4 g of trehalose was dissolved in 80 ml of 200 mM citric acid, pH 4.5, 5 mM EDTA; 1 g of agarose was added, and the mixture was melted in a microwave oven and then cooled to 50° C. Immediately before pouring the mixture onto the replica-plated colonies, 2 ml of N-ethylmaleimide (2.5 mg/ml), 985 units of horseradish peroxidase (EC 1.11.1.7), 800 units of glucose oxidase (EC 1.1.3.4), and 4.8 ml of o-dianisidine (10 mg/ml) were added. The overlay-assay mixture was incubated on the plates for 15 minutes at 24° C. Colonies with secreted acid trehalase activity developed a dark green color whereas the other transformants remained white.

Assays: liquid trehalase assays were performed as described previously (Kopp et al., 1993). Proteinase A was assayed according to Wiemken et al. (Wiemken et al., 1979), using denatured hemoglobin.

Amplification of Plasmid Library: a YEp24 genomic plasmid library (Carlson and Botstein, 1982) was kindly provided by D. Botstein (Stanford University). Amplification of the library was performed as described previously (Kopp et al., 1993).

Cloning, Sequencing and DNA Analysis of ATH1: genomic and plasmid DNA from *S. cerevisiae* and plasmid DNA from *E. coli* were prepared as described previously (Birnboim and Doly, 1979; Sherman et al., 1979). Standard procedures were followed for subcloning DNA fragments and for identifying recombinant clones (Maniatis et al., 1982). After screening for secreted acid trehalase activity, plasmid DNA from the positive-reacting yeast transformant colonies was isolated (Sherman et al., 1979); plasmids containing 8.5 and 10-kbp inserts were recovered. To determine the nucleotide sequence, SalI and EcoRI restriction fragments from the 8.5-kbp insert were subcloned into the vectors pTZ18R and pTZ19R (Pharmacia, Freiburg, Germany) to construct plasmids pMATZ1 to pMATZ4. The nucleotide sequence was determined by the dideoxy chain termination method (Sanger et al., 1977). The sequence containing the ATH1 gene was determined on both the coding and noncoding strands.

The 0.3 kb EcoRI/SalI fragment from pDAT1.9 was used as a probe in Southern (Southern, 1975) and Northern blot analyses. Radiolabeled DNA hybridization probes were prepared by the random priming method (Feinberg and Vogelstein, 1983). For Southern blot analysis, the genomic DNA was digested with EcoRI, separated on a 0.8% agarose gel, incubated in 0.25M HCl, and blotted onto a Hybond N⁺ membrane in 0.4M NaOH. For Northern blot analysis, the RNA was prepared by the method of Chirgwin (Chirgwin et al., 1979). Following electrophoresis, the RNA was transferred to a Hybond N⁺ membrane in 0.04M NaOH.

Deletion of ATH1: Plasmid pMATZ1 contains two EcoRV sites, one in the 5' non-coding region and the other within the open reading frame (FIG. 4). This plasmid was restricted with EcoRV to remove a 2.4-kbp fragment encoding most of the open reading frame of ATH1. The 1.1-kbp HindIII fragment containing the URA3 gene was isolated from plasmid YEp24, and the overhanging 5'-ends were filled in by treatment with the Klenow fragment of DNA polymerase I. The blunt-ended URA3 fragment was cloned into pMATZ1 which had been digested with EcoRV to generate plasmid pMATZ1.1. The EcoRI fragment from plasmid pMATZ1.1 was isolated and used to transform yeast strain SEY6210 with approximately 10 μg of DNA. Ura⁺ colonies were isolated and examined by Southern blotting to confirm the site of integration. Yeast strain MDY3 contained the URA3 gene integrated at the chromosomal ATH1 locus.

Identification of two ATH-secreting clones: in order to clone the structural gene encoding the vacuolar acid trehalase, we undertook two independent approaches. First, peptide sequences were obtained following the purification of a protein fraction with high acid trehalase activity (Mittenbühler and Holzer, 1988). Degenerate oligonucleotides were synthesized based on the peptide sequences and were used in a polymerase chain reaction with genomic DNA as template (Destruelle et al., 1994). Cloning of the corresponding gene led to the isolation of a novel yeast gene, YGP1 (Destruelle et al., 1994). The YGP1 gene codes for a highly glycosylated, secreted protein with an unknown function. The YGP1 gene, however, is not the structural gene for acid trehalase. It appears that additional proteins may have been retained during the initial purification (Mittenbühler and Holzer, 1988) of acid trehalase.

In the second approach, we relied on the observation that overproduction of vacuolar proteins can lead to their expression at the cell surface (Rothman et al., 1986; Stevens et al., 1986). Secreted proteins can then be identified by immunoblotting with a specific antibody or by their enzymatic activity. For the cloning of acid trehalase, we developed a specific enzymatic overlay assay that allowed the convenient screening of many transformants (see Materials and Methods). The activity of neutral trehalase was inhibited by the addition of 5 mM EDTA and the acidic pH of 4.5, where the enzyme shows very little activity (App and Holzer, 1989). To identify putative ATH-encoding clones, yeast strain SEY6210 was transformed with plasmid DNA from a YEp24-based genomic library (Carlson and Botstein, 1982). Between 200 and 500 transformant colonies per plate were replica-plated on YNB-plates containing fructose as a carbon source and assayed for secreted acid trehalase activity. In a screen of approximately 10,000 Ura⁺ transformants, nine were positive for secreted ATH activity. Reintroducing the purified plasmids (pDAT1.1-pDAT1.9) into yeast resulted in the secretion of acid trehalase activity. Thus, pDAT1.1-pDAT1.9 carry DNA sequences that cause yeast cells to secrete a catalytically active portion of their acid trehalase.

Analysis of the DNA fragment that confers an ATH secretion phenotype: Restriction mapping of the plasmid DNA isolated from the yeast cells revealed two types of plasmids with overlapping genomic inserts of 10 and 8.5-kbp. The plasmids were named pDAT1.8 and pDAT1.9, respectively. To define the limits of the DNA segment leading to acid trehalase secretion, various subclones of pDAT1.9 were constructed in plasmids YEp24 and pSEY8 (Emr et al., 1986), and yeast transformants carrying the subcloned plasmids were examined for secretion of ATH. None of the subclones showed secreted acid trehalase activity indicating that the functional gene sequence was larger than that contained on any of the subcloned fragments. Therefore, the entire nucleotide sequence of the 8.5-kbp insert was determined by sequence analysis. For that purpose, the EcoRI and SalI-fragments from the genomic insert of pDAT1.9 were subcloned into the sequencing vectors pTZ18R and pTZ19R. Analysis of the sequence revealed two open reading frames from which one has been described previously as part of the YMN1 gene (Thorsness et al., 1993). The second open reading frame (SEQUENCE ID NO:1), which showed no homology to sequences in the EMBL and GenBank nucleotide libraries, was 3,126 bp and is contained in the EcoRI fragment from pDAT1.9.7. The 5' noncoding region contains two possible TATA boxes. The open reading frame encodes a 1,041 amino acid protein (SEQUENCE ID NO:2) with a predicted molecular mass of approximately 117,400 Da. The coding region contains 25 potential N-glycosylation sites. The gene was named ATH1 (Accession Number: X84156 S. cerevisiae ATH1 gene), for yeast acid trehalase.

Characterization of ATH1: The amino acid sequence deduced from the ATH1 gene was compared with those of proteins in the SWISS-Prot and PIR protein databases by use of the FASTA algorithm and the Word search program of the University of Wisconsin Genetics Computer Group package (Devereux et al., 1984). This analysis did not reveal any homology to the five cloned trehalases from different organisms (Gutierrez et al., 1989; Kopp et al., 1993; Ruf et al., 1990; Su et al., 1993; Takiguchi et al., 1992) nor to any other protein in the libraries. Ath1p lacks a characteristic signal sequence at the amino terminus as expected for a soluble secretory pathway protein. In addition, there are no hydrophobic domains that are likely to serve as internal signal sequences. The deduced amino acid sequence also does not reveal a consensus signal sequence cleavage site based on the rules of von Heijne (von Heijne, 1986); there are no positive S values indicating likely cleavage sites within the first N-terminal 300 amino acids. However, localization of Ath1p to the vacuole could occur by a mechanism independent of the secretory pathway (Klionsky et al., 1992). ATH has been characterized as a glycosylated protein that transits to the vacuole in a sec-dependent manner, however, suggesting movement through the secretory pathway (Londesborough and Varimo, 1984; Harris and Cotter, 1988; Mittenbühler and Holzer, 1988).

To confirm the requirement of the ATH1 gene for acid trehalase activity, we carried out a one step gene transplacement (Rothstein, 1983). The ATH1 gene was disrupted at the chromosomal locus to generate the mutant yeast strain MDY3. The mutant strain has no detectable acid trehalase activity as determined using the overlay assay or liquid assays with crude cell extracts (Table 1).

TABLE 1

Enzymatic activities of vacuolar and cytosolic proteins in wild type strains and a strain overexpressing the ATH1 gene.

| Strain | ATH activity (mU/mg) | NTH activity (mU/mg) | Akaline phosphatase activity (mU/mg) | Glucose-6-phosphate Proteinase A dehydrogenase activity (mU/mg) |
|---|---|---|---|---|
| SEY6210 | 8.5 | 19.5 | 100 | 8.6160 |
| SEY6210/ YEp24 | 6.5 | 20.1 | 60 | 7.5175 |
| SEY6210/ pDAT1.9 | 67.0 | 26.1 | 70 | 7.6200 |

These results indicate that the ATH1 gene product is required for ATH activity but do not demonstrate whether ATH1 is the structural gene for acid trehalase or encodes a regulatory protein.

Northern blot analysis revealed that ATH1 is expressed in stationary phase cells while no expression could be detected in logarithmically growing yeast cells. The expression pattern corresponds with the activity profile of acid trehalase. To further investigate if ATH1 is the structural gene for acid trehalase or a putative regulator, activities of different vacuolar and cytosolic enzymes were measured in the acid trehalase-overproducing strain, the mutant strain MDY3 and in a wild type strain. As shown in Table 1, cells containing pDAT1.9 exhibit about an 8–10 fold higher level of acid trehalase activity than the same strain carrying the parent 2 μ plasmid YEp24. Of the enzyme activities examined, only acid trehalase is dramatically increased in cells containing pDAT1.9; the activities of other vacuolar proteins (alkaline phosphatase and proteinase A) and a cytosolic protein (glucose-6-phosphate dehydrogenase) are not elevated. The activity of neutral trehalase is slightly increased upon overproduction of ATH1. In the Δath1 strain, however, ATH activity is completely eliminated while there is no effect on NTH activity. The enzymatic activities of acid and neutral trehalases in the Δath1 strain are at the same levels as are seen in an acid trehalase mutant generated by random mutagenesis with ethyl methane sulfonate (Destruelle, 1993); the mutation completely eliminates ATH activity while having no effect on the activity of NTH. The plasmid pDAT1.9 complements the mutagen-induced defect but is not able to complement a mutant lacking neutral trehalase activity (Destruelle, 1993).

References

App and Holzer (1989) *J. Biol. Chem.* 264:17583–17588; Arguelles (1994) *FEBS Lett.* 350:266–270; Birnboim and Doly (1979) *Nucl. Acids Res.* 7:1513–1523; Carlson and Botstein (1982) *Cell* 28:145–154; Casadaban and Cohen (1980) *J. Mol. Biol.* 138:179–207; Chirgwin et al., (1979) *Biochemistry* 18:5294–5299; Destruelle (1993) Ph.D. thesis, Faculty of Biology, University of Freiburg, Germany; Destruelle et al., (1994) *Mol. Cell Biol.* 14:2740–2754; Devereux et al., (1984) *Nucl. Acid. Res.* 12:387–395; Elbein (1974) *Adv. Carbohydr. Chem. Biochem.* 0:227–256; Emr et al., (1986) *J. Cell Biol.* 102:523–533; Feinberg et al., (1983) *Anal. Biochem.* 132:6–13; Gelinas et al., (1989) *Appl. Environ. Microbiol.* 55:2453–2459; Guarente (1984) *Cell* 36:285–315; Gutierrez et al., (1989) *Mol. Gen. Genet.* 217:347–354; Harris and Cotter (1987) *Current Microbiol.* 15:247–249; Harris and Cotter (1988) *Can. J. Microbiol.* 34:835–838; Hino et al., (1990) *Appl. Environ. Microbiol.* 56:1386–1391; Ito et al., (1983) *J. Bacteriol.* 153:163–168; Klionsky et al., (1992) *J. Cell Biol.* 119, 287–299; Kopp et al., (1993) *J. Biol. Chem.* 268:4766–4774; Londesborough and Varimo (1984) *Biochem. J.* 219:511–518; Maniatis et al., (1982) *Molecular Cloning: A Laboratory Manual* Cold Spring Harbor Laboratory Press, New York; Mansure et al., (1994) *Biochem. Biophys. Acta* 1191:309–316; Miller (1972) *Experiments in molecular genetics* Cold Spring Harbor Laboratory Press, New York; Mittenbühler and Holzer (1988) *J. Biol. Chem.* 263:8537–8543; Mittenbühler and Holzer (1991) *Arch. Microbiol.* 155:217–220; Nwaka et al. (1994) *FEBS Lett.* 344:225–228; Oda et al., (1986) *Appl. Environ. Microbiol.* 52:941–943; Rine (1991) *Methods Enzymol.* 194:239–251; Rothman (1986) *Proc. Natl. Acad. Sci. USA* 83:3248–3252; Rothstein (1983) *Methods Enzymol.* 101:202–211; Ruf et al., (1990) *J. Biol. Chem.* 265:15034–15039; Sanger et al., (1977) *Proc. Natl. Acad. Sci. USA* 76:5463–5467; Sherman et al., (1979) *Methods in Yeast Genetics: A Laboratory Manual* Cold Spring Harbor Laboratory, Cold Spring Harbor Laboratory Press, New York; Southern (1975) *J. Mol. Biol.* 98:503–517; Stevens et al., (1986) *J. Cell Biol.* 102:1551–1557; Su et al., (1993) *Biochim. Biophys. Acta* 1173:217–224; Takiguchi et al., (1992) *Biochem. J.* 288:19–22; Thevelein (1984) *Microbiol. Rev.* 48:42–59; Thorsness et al., (1993) *Mol. Cell Biol.* 13:5418–5426; von Heijne (1986) *Nucl. Acids Res.* 14:4683–4690; Vuorio et al., (1993) *Eur. J. Biochem.* 216:849–861; Wickerham (1946) *J. Bacteriol.* 52:293–301; Wiemken (1990) *Antonie Van Leeuwenhoek* 58:209–217; Wiemken et al., (1979) *Arch. Microbiol.* 123:23–35; Wiggers (1832) *Ann. Pharm (Pozna)* 1:129–182; Winkler et al., (1991) *FEBS Lett.* 291:269–272.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated yeast mutant deficient in the expression of functional Ath1p gene product.

2. An isolated yeast mutant according to claim 1, wherein said mutant or an ancestor of said mutant was generated by genetically mutating a yeast cell to create a mutation in an Ath1p allele of said yeast cell.

3. An isolated yeast mutant according to claim 1, wherein said mutant expresses less than 10% of the functional Ath1p expressed by the corresponding wild-type yeast.

4. An isolated yeast mutant according to claim 1, which is *Saccharomyces Cerevisae* strain MDY3.

5. An isolated nucleic acid comprising ATH1 (SEQUENCE ID NO:1) or fragment thereof capable of hybridizing under stringent conditions with ATH1.

6. An isolated nucleic acid according to claim 5 comprising in 5'-3' orientation, a first ATH1 fragment thereof capable of hybridizing under stringent conditions with ATH1, an intervening sequence, and a second different ATH1 fragment thereof capable of hybridizing under stringent conditions with ATH1.

7. A method for producing a yeast mutant with improved survival ability under stress conditions, said method comprising steps:

subjecting a population of yeast to stress conditions;

detecting in said population a yeast mutant deficient in the expression of functional Ath1p gene product;

isolating said yeast mutant; and, growing said yeast mutant to obtain yeast with improved survival ability under stress conditions.

8. A method according to claim 7, said detecting step comprises contacting said population with an Ath1p gene product-specific reagent.

9. A method according to claim 7, said detecting step comprising contacting said population with an isolated nucleic acid comprising ATH1 (SEQUENCE ID NO:1) or fragment thereof capable of hybridizing under stringent conditions with ATH1.

* * * * *